United States Patent [19]
Miwa et al.

[11] 4,414,850
[45] Nov. 15, 1983

[54] MEASUREMENT METHOD AND SYSTEM UTILIZING ULTRASONIC WAVE

[75] Inventors: Hirohide Miwa, Kawasaki; Takaki Shimura, Machida; Keiichi Murakami, Kawasaki, all of Japan

[73] Assignee: Fujitsu Limited, Kawasaki, Japan

[21] Appl. No.: 269,861

[22] Filed: Jun. 3, 1981

[30] Foreign Application Priority Data

Jun. 3, 1980 [JP] Japan .................................. 55-74680

[51] Int. Cl.³ ............................................. G01N 29/00
[52] U.S. Cl. ....................................... 73/599; 73/602; 128/660
[58] Field of Search ................. 73/599, 602, 614, 620, 73/624, 625, 627, 628, 629; 128/660

[56] References Cited

U.S. PATENT DOCUMENTS

| | | | |
|---|---|---|---|
| 3,156,110 | 11/1964 | Clynes | 73/628 |
| 3,603,919 | 9/1971 | Moore | 367/93 |
| 4,057,049 | 11/1977 | Hill | 73/599 |
| 4,176,658 | 12/1979 | Kossoff et al. | 73/599 |
| 4,228,804 | 10/1980 | Holasek et al. | 73/602 |

FOREIGN PATENT DOCUMENTS

| | | |
|---|---|---|
| 52-2479 | 7/1977 | Japan . |
| 52-24798 | 7/1977 | Japan . |
| 56-37820 | 9/1981 | Japan . |

OTHER PUBLICATIONS

J. P. Jones, "Quantitative Characterization of Tissue Using Ultrasound", *IEEE Transaction on Nuclear Science*, vol. NS-27, No. 3, pp. 1168-1175, Jun. 1980.
J. P. Jones et al., "Computerized Data Analysis System for Ultrasonic Tissue Characterization", *Acoustical Imaging*, vol. 9, pp. 503-512, 1979.
A. C. Kak et al., "Signal Processing of Broadband Pulsed Ultrasound:Measurement of Atten. of Soft Bio. Tissues", IEEE Transaction on Biomedical Eng., vol. BME-25, No. 4, pp. 321-344, Jul. 1978.
J. Acoust. Soc. AM., "Comprehensive Compilation of Empirical Ultrasonic Properties of Mammalian Tissues", by Goss et al., Aug. 1978, pp. 423-457.
IEEE Ultrasonic Symposium Proceedings, "Parametric Estimation of the Acoustic Attenuation Coefficient Slope for Soft Tissue", 1976, pp. 44-47.
N.B.S. Special Publication, "Reflection Techniques for Measurement of Attenuation and Velocity", Paper 4.5, by G. Kossoff, Oct. 1976, pp. 135-139.

*Primary Examiner*—Stehen A. Kreitman
*Attorney, Agent, or Firm*—Staas & Halsey

[57] ABSTRACT

A measurement method and system for measuring characteristics of attenuation of domains in an object comprises transmitting ultrasonic waves into the object and receiving ultrasonic waves reflected from the object. The measured characteristics of attenuation of reflected waves is determined using signal intensities. A plurality of ultrasonic waves having different frequencies are transmitted either simultaneously or alternately to an object, and the reflected waves are received from the object. The signal intensities corresponding to the transmission frequencies among the reflected waves are stored and the signal intensity ratio is calculated. The signal intensity ratio indicates the attenuation characteristic. The attenuation coefficient can also be obtained using a time interval from the transmission time to the time of the reflected wave is received. The attenuation slope can be obtained from this attenuation coefficient and the frequency difference between transmitted ultrasonic waves.

20 Claims, 9 Drawing Figures

MEASUREMENT METHOD AND SYSTEM UTILIZING ULTRASONIC WAVE

BACKGROUND OF THE INVENTION

1. Field of the Invention

The present invention relates to a measurement system utilizing ultrasonic waves for measuring the attenuation characteristics of internal structures, such as organs within the human body, and particularly to a measurement method and system utilizing ultrasonic waves for diagnosis of the internal organs of a human body.

2. Description of the Prior Art

In the field of medical diagnostic technology and metal flaw detector technology, etc., ultrasonic wave image technology is widely employed, wherein the condition of a domain, for example, the location of the boundary from the beam transmitting location is displayed by transmitting the ultrasonic wave beam to an object and receiving and analyzing the wave reflected from the boundary of a domain within an object. The transmitted wave is attenuated in accordance with the internal structure characteristics of an object and is returned as the reflected wave after being influenced so as to contain characteristics indicative of the reflective coefficient of the boundary. Therefore, the attenuation characteristics of the internal structure can be measured by analyzing such a reflected wave in relation to the transmitted wave. Such technology is introduced in the Japanese Laid-Open Patent Specification No. 49-38490 (corresponding to Japanese Published Patent Specification No. 56-37820) or Japanese Published Patent Specification No. 52-24798. These prior art examples disclose that ultrasonic waves having a plurality of frequencies are emitted, the sonic pressure of each frequency is obtained from the received reflected wave, and then the attenuation characteristics of the internal structure are obtained from the ratio of such sonic pressures. However, with respect to the sonic pressure ratio, a large amount of error is usually introduced. That is, in these prior art examples, the phases of each component of the reflected wave differ when these are received from a heterogeneous medium such as a human body, and errors are included in the reflected wave received resulting from the so-called phase cancellation. Therefore, these prior art examples have the problem that an accurate attenuation characteristic cannot still be obtained even by the sonic pressure ratio.

SUMMARY OF THE INVENTION

It is an object of the present invention to provide an improved measurement method utilizing ultrasonic waves for accurately measuring the attenuation characteristics.

It is another object of the present invention to provide a measurement method utilizing ultrasonic waves for measuring the attenuation characteristics without being influenced by the phase cancellation effect of reflected waves.

It is a further object of the present invention to provide an improved measurement method utilizing ultrasonic waves for easily measuring attenuation characteristics.

It is another object of the present invention to provide a measurement method, utilizing ultrasonic waves, which is suitable for measuring attenuation characteristics of the internal structures of the human body.

It is a still further object of the present invention to provide a measurement method utilizing ultrasonic waves for measuring the attenuation characteristics on the basis of reflected signal intensity.

According to the present invention, the ultrasonic waves containing a plurality of frequencies are transmitted and the reflected waves obtained from an object are received in accordance with the ultrasonic waves transmitted. The intensity of a reflected wave, namely, the energy of it, is used for measurement and the ratio of intensities of reflected waves corresponding to respective transmission frequency bands determines the attenuation characteristics of an object. Since the energy of a reflected wave is not influenced by its phases, it is essential to receive the reflected wave containing accurate attenuation characteristics and to use the intensity of the reflected wave instead of the sonic pressure. For this purpose, an acousto-electric element, such as CdS, can be used as the receiving transducer, and a piezoelectric element such as PZT etc., segmented finely can be used to generate an intensity output by providing the square-calculation circuit for every segment and summing together the squared outputs. Typical attenuation characteristics thus obtained are the attenuation coefficient and the attenuation slope, which are displayed on the display as the attenuation characteristic distribution diagram of an object. The present invention is well understood by referring to the following embodiment of the present invention.

DESCRIPTION OF THE PREFERRED EMBODIMENTS

Figure 1:
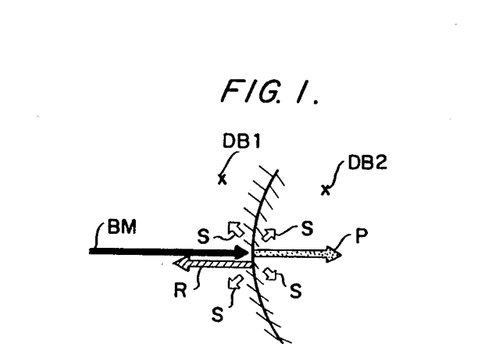
FIG. 1 and FIG. 2 schematically illustrate the principle of the present invention.
Figure 2:
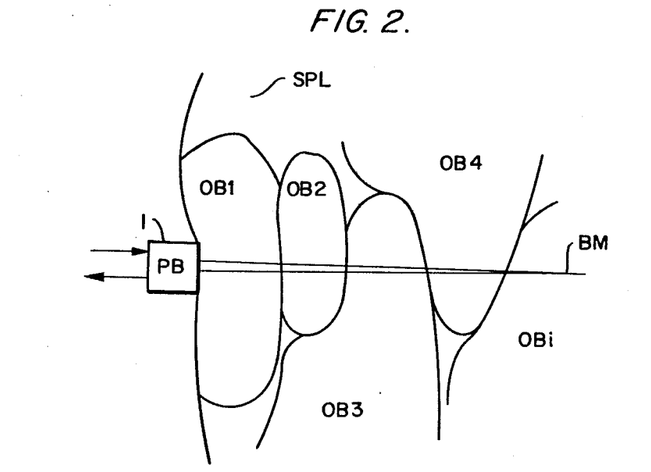
Figure 3:
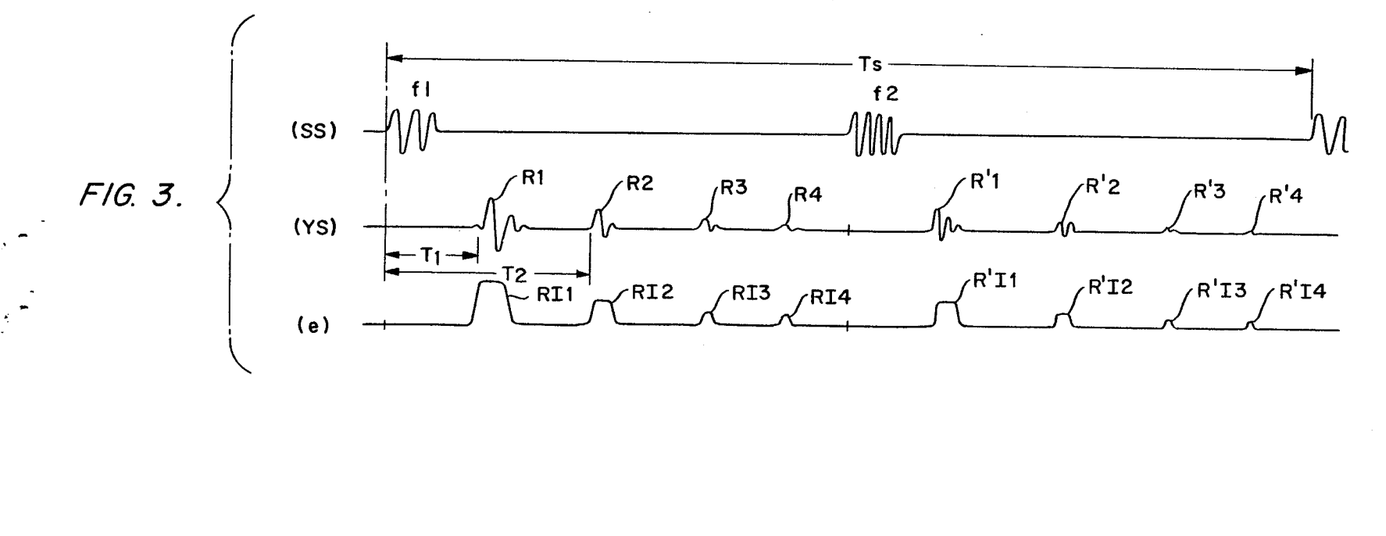
FIG. 3 is a graph illustrating the interrelation between transmitting and receiving signals of the present invention.

FIG. 1 and FIG. 2 each show the cross section of an object for explaining the principle of the present invention. FIG. 3 shows the time chart for these Figures. In the Figures, OB1, . . . , Obi are domains, SPL is the specimen as an object, PB is the transmit-receive element for transmitting and receiving ultrasonic waves (hereinafter referred to as a transducer), BM is the transmitted ultrasonic wave. In FIG. 1, the ultrasonic wave BM travelling through the domain OB1 is generally subjected to energy attenuation in the domain OB1, reflected and scattered at the boundary between the domains OB1 and OB2, and then the wave BM partly penetrates the boundary. When the intensity transmissivity at the boundary is considered to be P, the intensity reflection coefficient is R and the intensity scattering ratio combining all scattering direction is S, the following relation exists between the transmissivity, reflection coefficient and scattering ratio.

$$P + R + S = 1$$

In the above equation, it is known that the transmissivity, reflection coefficient and scattering ratio vary generally in accordance with the incident angle for the domain OB2 and the geometry, such as roughness and curvature, of the boundary surface, but such equation is also satisfied for different frequencies of transmitted ultrasonic waves. Moreover, if the ultrasonic wave BM is travelling in the direction opposite to that illustrated in FIG. 1, the above equation is also satisfied. In addition, attenuation of ultrasonic wave energy in the domain is expressed by the exponential function of path length. On the other hand, the attenuation coefficient is generally a function of ultrasonic wave frequency and is almost a linear function of frequency within the specified frequency range. Moreover, the propagation velocity of an ultrasonic wave does not depend on the frequency of the ultrasonic wave.

The principle of the present invention will be explained with reference to FIG. 2 and FIG. 3, on the basis of the following pre-conditions for ultrasonic waves. First, the symbols are defined as indicated below:

| | | |
|---|---|---|
| ○ | Intensity of transmitted ultrasonic wave: | I |
| ○ | Intensity of reflected wave which is reflected from the boundary between the domains OBi and OBi+1 and received at the transmitting location (hereinafter referred to as reflected intensity): | RIi (i = 1,2 ... ) |
| ○ | Intensity or attenuation coefficient of domain OBi: | $\mu$i (i = 1,2 ... ) |
| ○ | Path length of domain OBi: | li (i = 1,2 ... ) |
| ○ | Transmissivity at the boundary between the domains OBi and OBi+1: | Pi (i = 1,2 ... ) |
| | Reflection coefficient: | Ri (i = 1,2 ... ) |
| | Scattering ratio: | Si (i = 1,2 ... ) |
| ○ | Ultrasonic wave propagation velocity in the domain OBi: | Vi (i = 1,2 ... ) |

Here, intensity means a generally used instantaneous or time-integrated energy.

As the two frequency bands, two kinds of center frequencies $f_1$, $f_2$ are used and the attenuation coefficient $\mu$i and intensity I corresponding to the frequency $f_2$ are denoted by the superscript mark "'" for discrimination. The reflection coefficient Ri, transmissivity Pi and scattering ratio Si are the same respectively for the frequencies $f_1$, $f_2$ because they almost do not depend on the frequency at the specular boundary. The ultrasonic wave beams of frequencies $f_1$, $f_2$ are transmitted as SS of FIG. 3 from the transducer PB. The ultrasonic wave beam BM is reflected at the boundary between the domains OBi and OBi+1 and the reflected waves $R_1$, $R_2$, $R_3$, $R_4$ indicated in YS of FIG. 3 are received. These reflected waves correspond to those reflected from the mutual boundaries of OB1, OB2, OB3, OB4. The intensities RI1, RI2 of these signals $R_1$, $R_2$ are expressed as follows:

$$RI1 = I \cdot \exp(-\mu_1 \cdot l_1) \cdot R_1 \cdot \exp(-\mu_1 \cdot l_1) = I \cdot R_1 \cdot \exp(-2\mu_1 \cdot l_1)$$

$$RI2 = I \cdot \exp(-\mu_1 \cdot l_1) \cdot P_1 \cdot \exp(-\mu_2 \cdot l_2) \cdot R_2 \cdot \exp(-\mu_2 \cdot l_2) \cdot$$

-continued $$\bar{P}_1 \cdot \exp(-\mu_1 \cdot l_1) = I \cdot R_2 \cdot \exp\{-2(\mu_1 \cdot l_1 + \mu_2 \cdot l_2)\} \cdot P_1 \cdot \bar{P}_1$$

The general equation is expressed as follows.

$$RIi = I \cdot Ri \cdot \prod_{m=1}^{i} \{\exp(-2\mu_m \cdot l_m) \cdot P_{m-1} \cdot \bar{P}_{m-1}\} \quad (1)$$

Where, $P_0 = 1$.

Moreover, the intensity R'Ii of the signal R'i in case the ultrasonic wave beam of frequency $f_2$ is transmitted from the transducer PB is expressed by the following general equation.

$$R'Ii = I' \cdot Ri \cdot \prod_{m=1}^{i} \{\exp(-2\mu'_m \cdot l_m) \cdot P_{m-1} \cdot \bar{P}_{m-1}\} \quad (2)$$

Therefore, the ratio of intensity I of ultrasonic wave transmitted and the received reflected signal intensity Ri is expressed as follows using natural logarithms. For the frequency $f_1$, $$\ln(RI_1/I) = -2\mu_1 \cdot l_1 + \ln(R_1) \quad (3)$$

$$\ln(RI_2/I) = -2\mu_1 \cdot l_1 - 2\mu_2 \cdot l_2 + \ln(R_2) + \ln(\bar{P}_1 \cdot P_1)$$

$$\ln(RI_i/I) = \sum_{m=1}^{i} \{-2\mu_m \cdot l_m + \ln(P_{m-1} \cdot \bar{P}_{m-1})\} + \ln(R_i)$$

In the same way, the generation equation for the frequency $f_2$ becomes as follows:

$$\ln(R'I_i/I') = \sum_{m=1}^{i} \{-2\mu'_m \cdot l_m + \ln(P_{m-1} \cdot \bar{P}_{m-1})\} + \ln(R_i) \quad (4)$$

Here, when a difference between the equations (3) and (4) is obtained, it is expressed by the following equation.

$$\ln(RI_i/I) - \ln(R'I_i/I') = \sum_{m=1}^{i} (-2\mu_m \cdot l_m) - \quad (5)$$

$$\sum_{m=1}^{i} (-2\mu'_m \cdot l_m) = \sum_{m=1}^{i} -2l_m \cdot (\mu_m - \mu'_m)$$

The left side of equation (5) is obtained by measuring the intensities I, I' of ultrasonic waves of frequency bands $f_1$, $f_2$ and the reflected intensities RI, R'I. Here, $l_m$ in the right side is obtained as follows. When the propagation velocity Vi in the domain OBi is used, the period Ti from the time of transmitting the ultrasonic wave signal I to the time of receiving the reflected wave R is expressed by the following equation.

$$T_1 = \frac{2l_1}{V_1}$$

$$T_2 = \frac{2l_1}{V_2} + \frac{2l_2}{V_2}$$

-continued
$$T_i = 2 \sum_{m=1}^{i} \frac{2l_m}{V_m}$$

Therefore, $\ln(RI_1/I) - \ln(R'I_1/I') = -T_1 \cdot V_1 \cdot (\mu_1 - \mu'_1)$ $$\ln(RI_2/I) - \ln(R'I_2/I') =$$
$$T_1 \cdot V_1 \cdot (\mu_1 - \mu'_1) - (T_2 - T_1) \cdot V_2 \cdot (\mu_2 - \mu'_2) =$$
$$\ln(RI_1/I) - \ln(R'I_1/I') - (T_2 - T_1) \cdot V_2 \cdot (\mu_2 - \mu'_2)$$

The general equation is expressed as follows:

$$\ln(RI_i/I) - \ln(R'I_i/I_i) = -V_i(T_i - T_{i-1}) \cdot (\mu_i - \mu_i') + \ln(RI_{i-1}/I) - \ln(R'I_{i-1}/I') \quad (7)$$

In addition, the following equation can be obtained from the equation (7).

$$\ln\left(\frac{RI_i}{R'I_i} \cdot \frac{I'}{I}\right) = -V_i \cdot (T_i - T_{i-1}) \cdot (\mu_i - \mu_i') + \ln\left(\frac{RI_{i-1}}{R'I_{i-1}} \cdot \frac{I'}{I}\right) \therefore V_i \cdot (\mu_i - \mu_i') = \left\{\ln\left(\frac{RI_{i-1}}{R'I_{i-1}} \cdot \frac{I'}{I}\right) - \ln\left(\frac{RI_i}{R'I_i} \cdot \frac{I'}{I}\right)\right\} / (T_i - T_{i-1}) \quad (8)$$

Here, since the transmission intensities I, I' are known and the reflected receiving signal intensities $RI_i$, $R'I_i$, $RI_{i-1}$, $R'I_{i-1}$ and times $T_i$, $T_{i-1}$ can be actually determined by measurement, the value $V_i(\mu_i\mu'_i)$ can be obtained by an arithmetic operation. In equation (8), the propagation velocity in the internal structure can be approximated almost to a constant $V_0$ and when the intensities I, I' of beams in respective frequencies are constant $I_0$, the value $(\mu_i - \mu'_i)$ can be simplified as follows:

$$\mu_i - \mu'_i = \frac{\ln(RI_1/R'I_1)}{T_i \cdot V_0}$$

Therefore, the general expression becomes as follows:

$$\mu_i - \mu'_i = -\frac{1}{V_0} \cdot \frac{1}{T_i - T_{i-1}} \left(\ln\frac{RI_i}{R'I_i} - \ln\frac{RI_{i-1}}{R'I_{i-1}}\right) \quad (9)$$

Namely, when the reflected receiving signal intensities RI, R'I for the transmitting waves of respective frequencies and the time T are measured, the value of $(\mu_i - \mu'_i)$ can be obtained since the propagation velocity $V_0$ is known. Moreover, the attentuation slope $\alpha$ is obtained below. It is known that when attenuation slope $\alpha$ is expressed using the transmitting frequency f(MHz) and the attenuation coefficient $\mu$, the attenuation slope $\alpha$ (db/cm.MHz) used in general becomes as follows:

$$\alpha = 4.343(\mu/f)$$

Therefore, when the value $(\mu_i - \mu'_i)$ obtained by the calculation is used, the attenuation slope $\alpha$ can be expressed as follows:

$$\alpha = 4.343 \times \frac{\mu_i - \mu'_i}{f_1 - f_2} \quad (10)$$

Therefore, the following equation can be obtained by substituting the equation (9) into the equation (10).

$$\alpha = \frac{-1}{V_0} \cdot 4.343 (f_1 - f_2)^{-1} (T_i - T_{i-1})^{-1} \cdot \left(\ln\frac{RI_i}{R'I_i} - \ln\frac{RI_{i-1}}{R'I_{i-1}}\right) \quad (11)$$

It is also known that the intensity attenuation slope $\alpha$ of the internal anatomical structures is as follows:

| | |
|---|---|
| Adipose tissue | 1.26 (dB/cm MHz) |
| Blood | 0.36 (dB/cm MHz) |
| Liver | 1.88 (dB/cm MHz) |
| Kidney | 2.0 (dB/cm MHz) |

It has become possible to define the nature of each domain in the sample SPL from this measured attenuation slope $\alpha$ and the above table. For example, it is possible to detect and identify the abnormal portions such as cancer organization, etc. In the equation (11), $(T_i - T_{i-1})$ is the receiving interval of reflected signals, and it can be generated from an output by providing a means for detecting the receiving interval. It is more effective when the distributing condition is identified by displaying the attenuation slope $\alpha$ or attenuation coefficient $(\mu_i - \mu'_i)$ or the value $V_i \cdot (\mu_i - \mu'_i)$ as the distributed images on the screen.

As explained above, in the present invention, the attention is focused on the intensity of reflected wave, namely the instantaneous energy value or the pulse width time integrated energy and therefore the present invention provides accurate measurement without any influence of the phase cancellation effect. The energy value of a reflected wave can be output by various methods. In one method, the acousto-electric element such as CdS which converts sonic energy into electron flow is used as the receiving transducer. In this case, energy of reflected wave can directly be output.

In another method, a piezoelectric element such as PZT which converts sonic pressure into a voltage is used as the receiving transducer. Thereby, voltage converted from sonic pressure can then be converted into energy by the square calculation. In addition, the influence of phase cancellation can be eliminated perfectly by dividing the receiving surface of the piezoelectric element into many minute segments and by providing the square-calculation circuits corresponding to each segment and summing together all the outputs.

Figure 4:
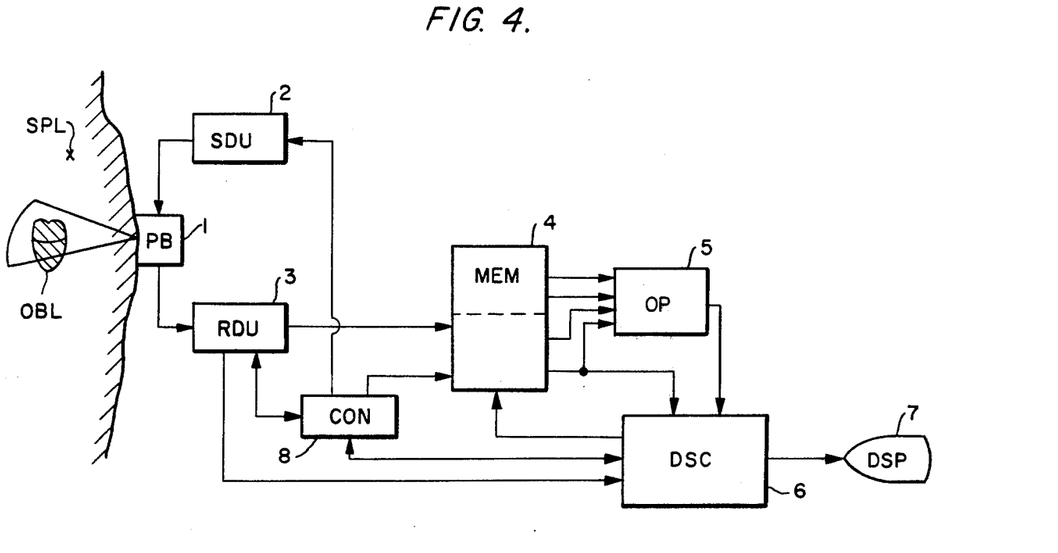
FIG. 4 is a block diagram of an embodiment of the present invention.

The system of the present invention is explained with reference to FIG. 4 to FIG. 8 hereunder. In FIG. 4, the reference numeral 1 is the transducer, which transmits the ultrasonic wave beam and receives such reflected waves, and then scans the domain by changing the transmitting direction upon completion of each transmit/receive operation of ultrasonic waves of a pair of frequencies. A transmit unit 2 oscillates the transducer 1 to provide different frequency bands. A receive unit 3 discriminates the reflected signal from the received output of transducer 1 and outputs the data indicating the intensity of the received signal and data indicating the time from the received signal to the next reflected signal. A memory unit 4 sequentially stores the output data of receive unit 3. An operation unit 5 performs calculations in accordance with the equations (9) and (11) explained above and outputs the data identifying respective domains. A display control unit 6 synchronizes with the receive timing of receive unit 3 and generates display data of the tomographic section on the basis of the data of the above-mentioned operation unit 5. A display unit 7 displays images of the CRT display device. A control unit 8 controls switching of transmission and reception, writing into the memory unit 4 and read out timing. The operation of the system is explained hereunder. The control unit 8 generates an output signal which is provided to the transmit unit 2 in order to drive the transducer 1 with the signal of frequency $f_1$. The transmit unit 2 outputs a signal by oscillating with the frequency $f_1$, causing the transducer 1 to send the ultrasonic wave beam of frequency $f_1$ to the specimen. When the control unit 8 sends the output signal to the transmit unit 2, it simultaneously generates a signal indicating the send timing to the receive unit 3. After receiving the send timing signal, the receive unit 3 starts measuring the time period until detecting the received reflected signal. In every timing that the signal over a certain threshold is received by the receive unit 3 via the transducer 1, the receive unit 3 considers this signal as the reflected signal and outputs the reflected data indicating the intensity of such signal and time data indicated by the time measuring operation, to the memory unit 4. The reflected data and time data are sequentially stored in the memory unit 4 on a time series basis. After the specified period, for example, the period longer than that required by the ultrasonic wave beam to enter and return from a section of the human body, the control unit 8 generates an output which oscillates the transmit unit 2 with the above-mentioned frequency $f_2$. The transmit unit 2 causes the transducer 1 to send the ultrasonic wave beam of frequency $f_2$ as explained previously. Meanwhile, the receive unit 3 stores the receive data in the memory unit 4 as explained above. Here, the transducer 1 is not always required to be used in common for transmission and reception and may be installed individually for transmission and reception. It is proposed that an acousto-electric transducer, such as a CdS transducer, can be used as a receiving transducer, and a piezoelectric element, such as PZT etc., segmented, finally can be used to generate an intensity output by providing a square calculation circuit for every segment and summing together the squared output. When the receive unit 3 has a structure that includes a filter (e.g. a bandpass filter) which can discriminate the reflected signals corresponding to plural frequency bands, it is also possible to simultaneously transmit and receive signals in plural frequency bands from a single transducer. Plural transducers may also be provided corresponding to the frequency bands. FIG. 9 illustrates an alternate embodiment of the invention in which plural transducers 1A, 1B and 1C corresponding to plural frequency bands, are employed.

Figure 5:
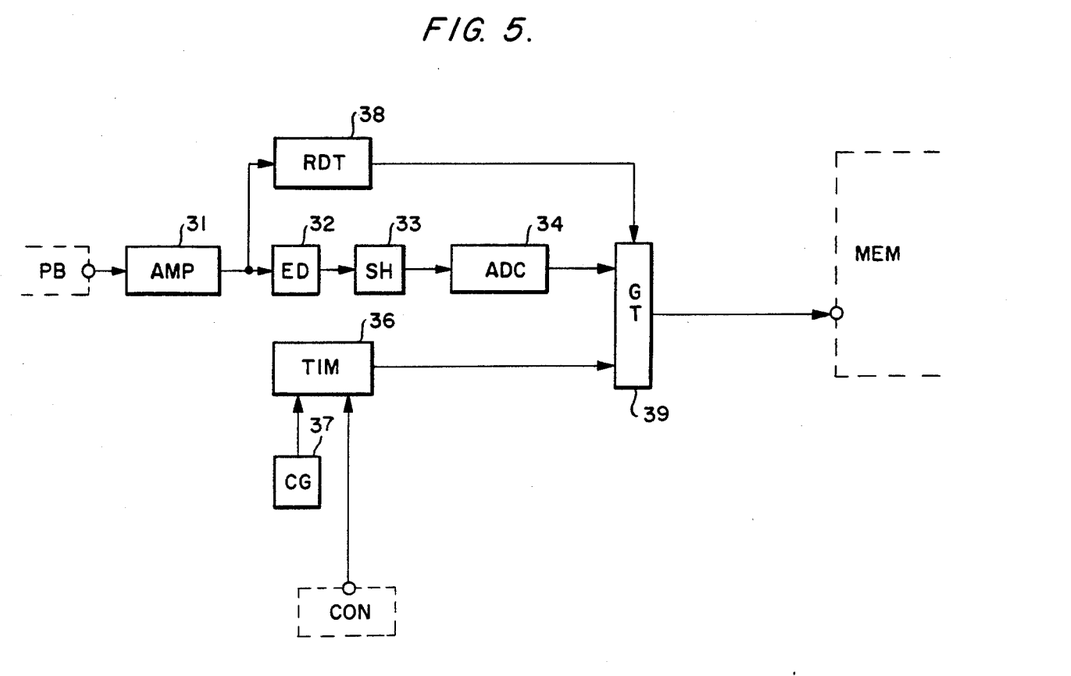
FIG. 5 is a detailed block diagram of the receiving circuit shown in FIG. 4.

FIG. 5 shows a specific block diagram of the receive unit 3. The operation of this unit will be explained below. The received signal indicated in FIG. 3 (YS) to be supplied from the transducer 1 is amplified by the amplifier 31. In case attenuation is large, the gain is gradually increased from the send timing so that attenuation from the deeper area is compensated; and it is recommended to store the required compensation amount in the memory unit. The amplified received signal is square-rectified in the envelope detector 32 and thereby, the envelope signal of FIG. 3(e) can be generated. The envelope signal (e) is subjected to sample holding at the sample and hold circuit SH using a sampling pulse having a very short period and is then converted to a digital value by an analog-to-digital converter 34. Meanwhile, the timer 36 starts time counting by receiving the send timing signal sent from the control unit 8, counts the clock pulses supplied from a clock generator 37 and outputs the counted value to the gate 39. The received signal amplified by the amplifier 31 is then input to a reflected signal detector 38. The reflected signal detector 38, having a specified slice level, considers a received signal higher than the slice level as the reflected signal of interest and outputs a detected pulse. This detected pulse is supplied to the gate 39, causing the gate 39 to open. Therefore, the reflected wave data of analog to digital converter 34 and the time data of timer 36 are supplied to the memory unit 4 via the gate 39 at the timing of the output of the detected pulse.

In FIG. 4, the reflected wave data and the time data corresponding to the beams of frequencies $f_1$ and $f_2$ stored in the memory unit 4 are read out to the operation unit 5. The operation unit 5 executes the operations of the equations (9) and (11) using this data, and then calculates an attenuation slope and outputs it.

Figure 6:
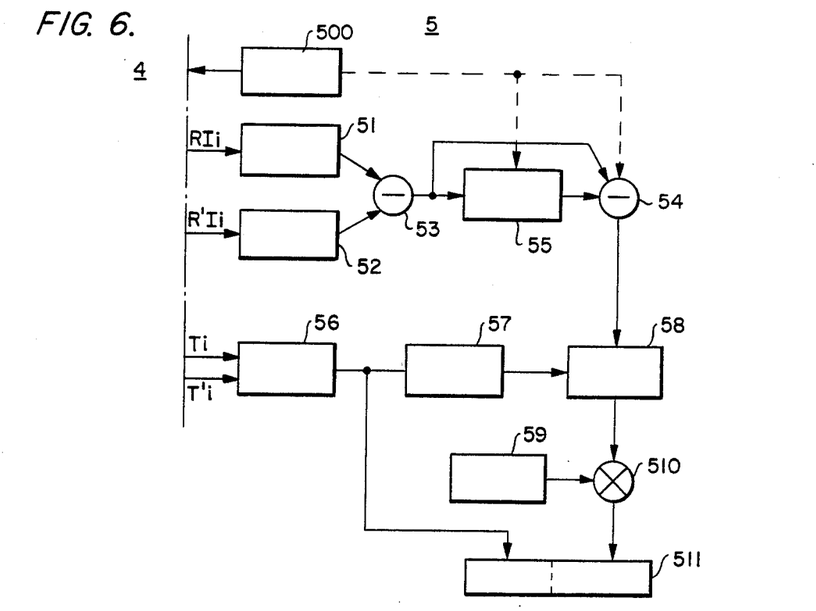
FIG. 6 is a detailed block diagram of the arithmetic operation circuit 5 shown in FIG. 4.

FIG. 6 shows the specific block diagram of the operation unit 5. The operation unit 5 provides a generator 59 which generates a constant value "$4.343/V_0(f_1-f_2)$" in above equation (11), and is so configured that these constants are set for each frequency of the ultrasonic wave beams to be transmitted. A timing control circuit 500 extracts the reflected wave data, namely the above-mentioned signals $RI_i$, $R'I_i$ corresponding to respective beams of memory unit 4 and the time data $T_i$. In other words, when analyzing the first reflected signal, the signals $RI_1$, $R'I_1$, $T_1$ are read out. The signals $RI_1$, $R'I_1$ are input to the natural logarithm circuits 51, 52 for logarithmic operations and the output logarithmic values are subtracted by means of a subtraction circuit 53. The output of the subtraction circuit 53 is the data indicating the values "ln $(RI_1/R'I_1)$". This data is supplied to the subtraction circuit 54. Meanwhile, the register circuit 55 is initially reset by a timing control circuit 500 and outputs data indicating a value "0". The subtraction circuit 54 subtracts the output data "0" of the register circuit 55 from the data indicating "ln $(RI_1/R'I_1)$" and therefore outputs the data indicating the value "ln $(RI_1/R'I_1)$". When the subtraction circuit 54 completes subtraction, the output data of subtraction circuit 53 is stored by the register circuit 55. Meanwhile, the time data $T_i$ is read by a read-out circuit 56. A time-difference generation circuit generates a value "$T_i-T_{i-1}$" for the equation (11) and supplies the time $T_1$ from the point of transmission until the first reflected signal $RI_1$ to the divider circuit 58. The divider circuit 58 divides the data "ln $(RI_1/R'I_i)$−ln $(RI_{i-1}/R'I_{i-1})$" by the value "$T_i-T_{i-1}$". The divided data is multiplied by the coefficient supplied from the above-mentioned generator 59 by a multiplier circuit 510 and the attenuation slope $\alpha$ is obtained. The attenuation slope $\alpha$ thus computed and the time data $T_i$ as the data related to the period of wave travel from the sending location to the boundary between the domain i having the attenuation slope $\alpha$ and the next domain i+1, are set in a register 511 and are then supplied to the display control unit 6 in FIG. 6.

In FIG. 4, the display control unit 6 identifies the tissue corresponding to the attenuation slope α on the basis of data transferred from the operation unit 5, and carries out a brightness modulation for the scan beam of indicator 70.

Figure 7:
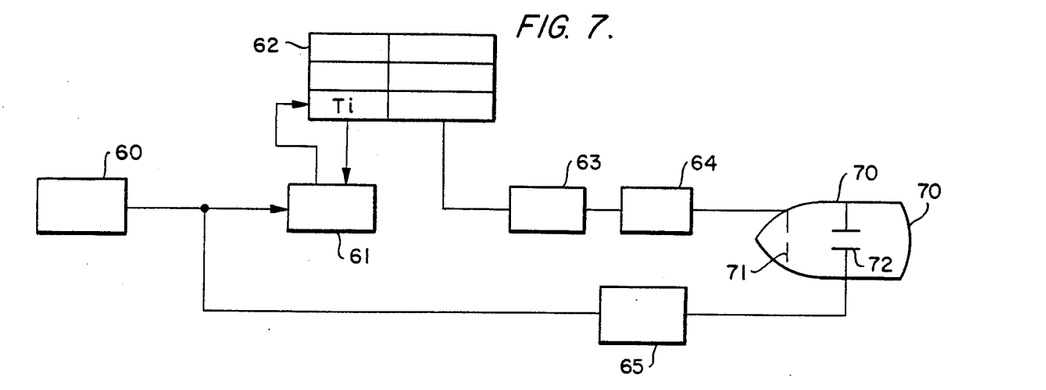
FIG. 7 is a detailed block diagram of the display control circuit 6 shown in FIG. 4.
Figure 8:
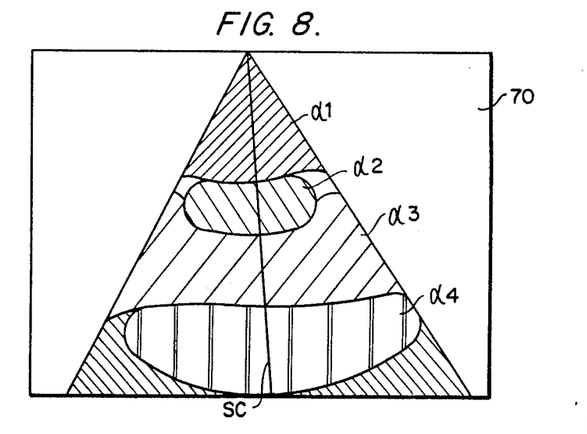
FIG. 8 is a distribution diagram of attenuation characteristics indicated by the present invention.
Figure 9:
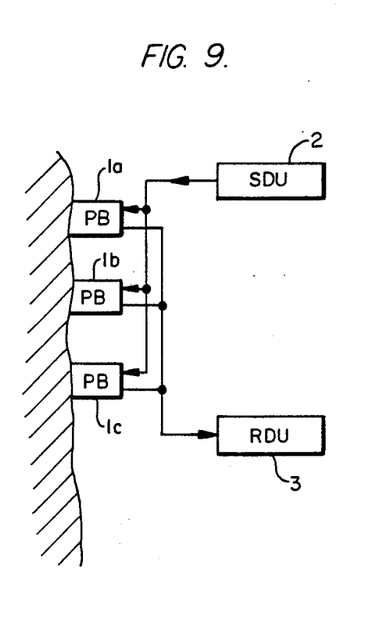
FIG. 9 is a block diagram of an alternate embodiment of the present invention in which plural transducers are employed.

FIG. 7 and FIG. 8 are detailed block diagrams of the display control unit 6 and the display screen 70 of the display unit 7 showing the attenuation distribution diagram. The display control unit 6 includes a counter 60. When the counter synchronizes the timer 36 of the receive unit 3 mentioned above, the scan period of one scanning line SC of the indicator 7 is placed in synchronization with the period required for receiving a pair of reflected ultrasonic waves. Namely, control is carried out in such a way that one scanning line SC is scanned during the send and receive period $T_s$ in the unit indicated in FIG. 3.

The operation of the display control unit 6 will be explained hereunder. A count value is sequentially counted by the counter 60 and is then supplied to the deflection control circuit 65. The deflection control circuit 65 causes the electron beam to scan by means of the beam deflection mechanism 72 of the display 7. The counted value of the counter 60 is then supplied to a comparator 61. Meanwhile, a buffer 62, which is composed of the first-in/first-out registers accumulating the attentuation slope α and time data in the display control unit 6 in the supply sequence, is provided and the time data is supplied to the comparator 61. In addition, the attenuation slope α is supplied to an attenuation constant table 63 and then converted to data for identifying a tissue type, e.g. cancer. This converted data is then supplied to a digital-to-analog converter 64 and displayed on a display screen by the brightness controller 71. When the comparator 61 detects matching of count value and time data, it reads the next time data and attenuation constant pair being stored in the buffer 62. This operation is repeated. In this manner, the scanning is carried out on the display 7 in synchronization with the scanning of a specimen by the transducer 1. A tomographic image including the domain $OB_1$, $OB_2$ . . . shown in FIG. 2 is discriminated by the brightness or color as indicated in FIG. 8.

In the above embodiment, respective domains are discriminated by the brightness or color, but, for example, the biological tissue type identified may also be indicated or printed out. In this case, it is necessary to provide a memory corresponding to the display screen in the display control unit 6 and to add processing such as writing the identified data into the memory.

As explained previously, the present invention offers the effect of accurately identifying the nature of respective domain in the specimen from the reflected signal.

We claim:

1. A measurement method utilizing ultrasonic waves for measuring attenuation characteristics of domains in an object, comprising the steps of:
   (a) transmitting ultrasonic waves of plural different frequencies to an object;
   (b) receiving the ultrasonic waves reflected from the object; and
   (c) measuring the attenuation characteristics of the domains on the basis of the ratio of intensities of the received reflected ultrasonic waves.

2. A measurement method utilizing ultrasonic waves as claimed in claim 1, wherein in step (a) the ultrasonic waves of plural different frequencies are alternately transmitted.

3. A measurement method utilizing ultrasonic waves as claimed in claim 1, wherein in step (a) the ultrasonic waves of plural different frequencies are simultaneously transmitted, and wherein said step (c) further comprises the step of separating the reflected ultrasonic waves corresponding to the frequencies of the transmitted ultrasonic waves from the received reflected ultrasonic waves.

4. A measurement method utilizing ultrasonic waves as claimed in claim 1, wherein said step (c) comprises the following substeps:
   (1) measuring an intensity ratio of the reflected waves;
   (2) measuring a time interval from the time the ultrasonic waves are transmitted to the time the reflected waves are received; and
   (3) measuring the attenuation characteristics from the measured time interval and the intensity ratio.

5. A measurement method utilizing ultrasonic waves as claimed in claim 4, wherein said substep (3) comprises further obtaining the attenuation characteristics from the difference in the plural frequencies.

6. A measurement method utilizing ulrasonic waves as claimed in claim 1, further comprising the step of:
   (d) displaying the attenuation characteristics as distributed images.

7. A measurement system utilizing ultrasonic waves for measuring attenuation characteristics of a domain in an object by transmitting the ultrasonic waves into the object and by receiving the ultrasonic waves reflected from the object, comprising:
   (a) ultrasonic wave transmit/receive means for transmitting the ultrasonic waves of different frequencies to the object and for receiving the ultrasonic waves reflected from the object; and
   (b) meansurement means, operatively connected to said ultrasonic wave transmit/receive means, for measuring attenuation characteristics of the domains from a signal intensity ratio corresponding to each of said different frequencies of the reflected ultrasonic waves received.

8. A measurement system utilizing ultrasonic waves as claimed in claim 7, wherein said ultrasonic wave transmit/receive means comprises:
   an ultrasonic wave transducer;
   a transmit circuit, connected to said ultrasonic wave transducer, for transmitting the ultrasonic waves; and
   a receive circuit connected to said ultrasonic wave transducer.

9. A measurement system utilizing ultrasonic waves as claimed in claim 7, wherein said ultrasonic wave transmit/receive means comprises:
   an ultrasonic wave transducer; and
   a transmit circuit, operatively connected to said ultrasonic wave transducer, for causing said ultrasonic wave transducer to transmit the ultrasonic waves of different frequencies simultaneously.

10. A measurement system utilizing ultrasonic waves as claimed in claim 8, wherein said transmit circuit comprises means for causing said ultrasonic wave transducer to transmit the ultrasonic waves of different frequencies alternately.

11. A measurement system utilizing ultrasonic waves as claimed in claim 8, wherein said transmit circuit comprises means for causing said ultrasonic wave transducer to transmit the ultrasonic waves of different frequencies simultaneously and wherein said receive circuit comprises means for separating the received ultrasonic waves corresponding to the frequencies of ultrasonic waves transmitted from the reflected ultrasonic waves received by said ultrasonic wave transducer.

12. A measurement system utilizing ultrasonic waves as claimed in claim 7, wherein said ultrasonic wave transmit/receive means comprises a transducer which is used in common for transmitting and receiving the ultrasonic waves.

13. A measurement system utilizing ultrasonic waves as claimed in claim 7, wherein said ultrasonic wave transmit/receive means comprises a transmit-only transducer and a receive-only transducer.

14. A measurement system utilizing ultrasonic waves as claimed in claim 8, wherein said ultrasonic wave transducer comprises a plurality of transducers each of which corresponds to one of the frequencies of the ultrasonic waves transmitted by said ultrasonic wave transmit/receive means.

15. A measurement system utilizing ultrasonic waves as claimed in claim 13, wherein said receive-only transducer comprises an acousto-electric element which output a signal corresponding to the reflected wave intensity.

16. A measurement system utilizing ultrasonic waves as claimed in claim 8, wherein said receive circuit comprises a circuit for converting the reflected wave signals output from said ultrasonic wave transducer into intensity signals corresponding to the reflected wave intensity.

17. A measurement system utilizing ultrasonic wave as claimed in claim 7, wherein said measurement means comprises:
a memory for storing data representing the signal intensity of the ultrasonic waves reflected from the object; and
operation means, connected to said memory, for calculating said signal intensity ratio.

18. A measurement system utilizing ultrasonic waves as claimed in claim 8, wherein said receive circuit comprises a circuit for outputting a time signal corresponding to the time interval from the time the ultrasonic waves are transmitted to the time the received reflected ultrasonic waves are received.

19. A measurement system utilizing ultrasonic waves as claimed in claim 18, wherein said measurement means comprises:
a memory for storing data representing the signal intensities of said received reflected ultrasonic waves and data representing said time signal; and
an operation circuit, connected to said memory, for calculating said signal intensity ratio and for calculating the attenuation characteristics by utilizing said data representing said time signal.

20. A measurement system utilizing ultrasonic waves as claimed in claim 7, further comprising display means, connected to said measurement means, for displaying the measured attenuation characteristics as distributed images.

* * * * *

UNITED STATES PATENT AND TRADEMARK OFFICE
CERTIFICATE OF CORRECTION

PATENT NO. : 4,414,850
DATED : NOVEMBER 15, 1983
INVENTOR(S) : HIROHIDE MIWA ET AL.

It is certified that error appears in the above-identified patent and that said Letters Patent is hereby corrected as shown below:

Col. 2, line 56, "Obi" should be --OBi--.

Col. 3, line 39, "li" should be --$\ell i$--;

line 66, "$1_1$" should be --$\ell_1$-- (all occurrences);

line 67, "$1_1$" should be --$\ell_1$--; and             "$1_2$" (both occurrences) should be --$\ell_2$--.

Col. 4, line 3, "$1_1$" should be --$\ell_1$-- (both occurrences); and

"$1_2$" should be --$\ell_2$--;

line 7, "$1_m$" should be --$\ell_m$--;

line 17, "$1_m$" should be --$\ell_m$--;

UNITED STATES PATENT AND TRADEMARK OFFICE
CERTIFICATE OF CORRECTION

PATENT NO. : 4,414,850  
DATED : NOVEMBER 15, 1983  
INVENTOR(S) : HIROHIDE MIWA ET AL.

Page 2 of 3

It is certified that error appears in the above-identified patent and that said Letters Patent is hereby corrected as shown below:

line 22, "Ri" should be --RI--;

line 25, "$l_1$" should be --$\ell_1$--;

line 27, "$l_1$" should be --$\ell_1$--; and "$l_2$" should be --$\ell_2$--;

line 32, "$l_m$" should be --$\ell_m$--;

line 38, "$l_m$" should be --$\ell_m$--;

line 46, "$l_m$" should be --$\ell_m$--;

line 49, "$l_m$" (both occurrences) should be --$\ell_m$--;

line 53, "$l_m$" should be --$\ell_m$--;

line 60, "$2l_1$" should be --$2\ell_1$--;

line 63, "$2l_1$" should be --$2\ell_1$--; and "$2l_2$" should be --$2\ell_2$--.

UNITED STATES PATENT AND TRADEMARK OFFICE
CERTIFICATE OF CORRECTION

PATENT NO. : 4,414,850

DATED : NOVEMBER 15, 1983

INVENTOR(S) : HIROHIDE MIWA ET AL.

It is certified that error appears in the above-identified patent and that said Letters Patent is hereby corrected as shown below:

Col. 5, line 2, "$2l_m$" should be --$2\ell_m$--;

line 5, "$(R'I_1/I')$" should be --$(R'I_1/I')$--;

line 36, "$(\mu_i\mu_i')$" should be --$(\mu_i-\mu_i')$--.

Col. 10, line 36, "meansurement" should be --measurement--.

Col. 11, line 23, "output" should be --outputs--.

Signed and Sealed this

Tenth Day of April 1984

[SEAL]

Attest:

GERALD J. MOSSINGHOFF

Attesting Officer

Commissioner of Patents and Trademarks